United States Patent

Isogai et al.

[11] Patent Number: 6,123,423
[45] Date of Patent: Sep. 26, 2000

[54] OPTHALMIC APPARATUS

[75] Inventors: Naoki Isogai, Nishio; Hiroyoshi Nakanishi, Aichi, both of Japan

[73] Assignee: Nidek Co., Ltd., Aichi, Japan

[21] Appl. No.: 09/433,015

[22] Filed: Nov. 3, 1999

[30] Foreign Application Priority Data

Nov. 4, 1998 [JP] Japan .................. 10-313149

[51] Int. Cl.⁷ .................. A61B 3/00
[52] U.S. Cl. .................. 351/200
[58] Field of Search .................. 351/200, 221, 351/222, 237, 246; 600/300; 128/903, 904; 706/10, 924

[56] References Cited

U.S. PATENT DOCUMENTS

| | | | |
|---|---|---|---|
| 5,892,570 | 4/1999 | Stevens | 351/237 |
| 5,943,116 | 8/1999 | Zeimer | 351/221 |
| 6,017,307 | 1/2000 | Raines | 600/300 |

Primary Examiner—George Manuel
Attorney, Agent, or Firm—Finnegan, Henderson, Farabow, Garrett & Dunner, L.L.P.

[57] ABSTRACT

An ophthalmic apparatus comprising a measurement unit and a peripheral unit each of which is contained in a separate housing, wherein the measurement unit includes a measurement device for measuring a characteristic of an eye to be examined and a sending device capable of sending a signal for sending measurement data obtained by the measurement device in an unformatted state for output, and the peripheral unit includes a receiving device for receiving the signal sent by the sending device, an output device for outputting the measurement data received by the receiving device, a storage device for storing output format data used to format the measurement data upon output by the output device and an output control device for formatting the measurement data using the output format data and for controlling the output device so as to produce output.

16 Claims, 2 Drawing Sheets

※ ⊔ indicates a space
※ ⏎ indicates a line feed

OPTHALMIC APPARATUS

BACKGROUND OF THE INVENTION

1. Field of the Invention

The present invention relates to an ophthalmic apparatus for measuring a characteristic of an eye to be examined.

2. Description of Related Art

As an ophthalmic apparatus for measuring a characteristic of an eye to be examined, a refractmeter, an ophthalmometer, a keratometer, a tonometer and the like are widely known. Recently, a hand-held type apparatus has been provided allowing an easy and convenient measurement regardless of a posture of a patient (for example, an infant or a patient lying on his back).

This type of apparatus is usually provided with a measurement unit including a measurement part, and with a peripheral unit (including a printer, an external computer, another ophthalmic apparatus and the like) separately. The two units are, for example, connected via cable to transmit measurement data therebetween or the data transmission is done via wireless communications using infrared rays or the like for the sake of grater operativity and mobility of the measurement unit. In the case of transmitting measurement data to an external computer via wireless communications, the measurement data is first transmitted to a printer and then transmitted to the external computer from the printer.

In the above-described conventional art, however, to transmit measurement data to a printer or the like, all the data is formatted entirely on the side of the measurement unit before the transmission. This results in a great amount of the data so that it takes longer for the transmission, and that possibility of occurrence of a transmission error is increased. This is disadvantageous especially in wireless communications using infrared rays or the like. Although it is possible to adopt high-speed communications to shorten transmission time in the case of wireless communications, there are disadvantages of increasing the cost and shorten the communications distance.

Further, in the case of a hand-held type apparatus, it is relatively inconvenient to manipulate such an apparatus to carry out wireless communications. That is to say, after obtaining necessary measurement data, an examiner is required to turn a measurement unit toward a receiving end of an output device such as a printer, and then hold down a transmission button or the like that the measurement unit has until the transmission is completed.

Still further, in the case of transmitting measurement data to an external computer via wireless communications, it is inconvenient to carry out the transmission by way of a printer. In recent years, there have been computers provided with an infrared communications facility. Yet, most of these computers are compliant with the IrDA (Infrared Data Association) standard, which is the International Standard for infrared communications. Therefore, the computers are incapable of communications between a measurement unit and a printer if they do not meet the IrDA compliant, but their special standard.

SUMMARY OF THE INVENTION

The present invention has been made in view of the above circumstances and has an object to overcome the above problems and to provide an apparatus capable of saving time required to transmit data between a measurement unit and a peripheral unit even in the case the two units are provided separately.

Another object of the present invention is to provide an apparatus capable of reducing the inconvenience of manipulating switches upon data communications from a measurement unit.

Further, another object of the present invention is to provide an apparatus enabling data communications with a peripheral unit which complies with a different standard for infrared communications.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus comprises a measurement unit and a peripheral unit each of which is contained in a separate housing. The measurement unit includes measurement means for measuring a characteristic of an eye to be examined, and sending means capable of sending a signal for sending measurement data obtained by the measurement means in an unformatted state for output. The peripheral unit includes receiving means for receiving the signal sent by the sending means, output means for outputting the measurement data received by the receiving means, storage means for storing output format data used to format the measurement data upon output by the output means, and output control means for formatting the measurement data using the output format data and for controlling the output means so as to produce output.

In another aspect of the present invention, an ophthalmic apparatus comprises a measurement unit and a peripheral unit each of which is contained in a separate housing. The measurement unit includes measurement means for measuring a characteristic of an eye to be examined, completion determination means for determining whether a measurement is completed, sending means capable of sending a signal via wireless communications for sending measurement data obtained by the measurement means, and transmission control means for controlling the sending means so as to send the measurement data automatically when the completion determination means determines that the measurement is completed. The peripheral unit includes receiving means capable of wireless communications for receiving the signal sent by the sending means, and output means for outputting the measurement data received by the receiving means.

Further, in another aspect of the present invention, an ophthalmic apparatus comprises a measurement unit and a peripheral unit each of which is contained in a separate housing. The measurement unit includes measurement means for measuring a characteristic of an eye to be examined, sending means capable of sending a signal via wireless communications for modulating and sending measurement data obtained by the measurement means to comply with a plurality of types of communications standards, and select means for selecting a type of the communications standard to be used in transmission. The peripheral unit includes receiving means capable of wireless communications for receiving the signal sent by the sending means, and output means for outputting the measurement data received by the receiving means.

As described above, according to the present invention, merely minimum data, the data which does not include any format data for output, is transmitted. Thus, both the time required to transmit the data and the occurrence of data transmission errors can be reduced.

In addition, in the case of wireless communications, since the data is transmitted automatically upon completion of a measurement, inconvenience of manipulating the switches is reduced. Since the measurement can be done with reducing the number of switch button manipulations required from starting of the measurement to external output, the amount of work in the measurement is reduced. This allows the examiner to concentrate on observing the state of the examinee's eye or on alignment, thereby increasing reliability of the measured values.

Further, by adopting bi-directional communications, errors occurred to the peripheral unit are checked on the side of the main apparatus, so that errors in the printout or in the external output may be prevented.

Still further, data communications to a peripheral unit that complies with a different standard for infrared communications may be handled easily.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
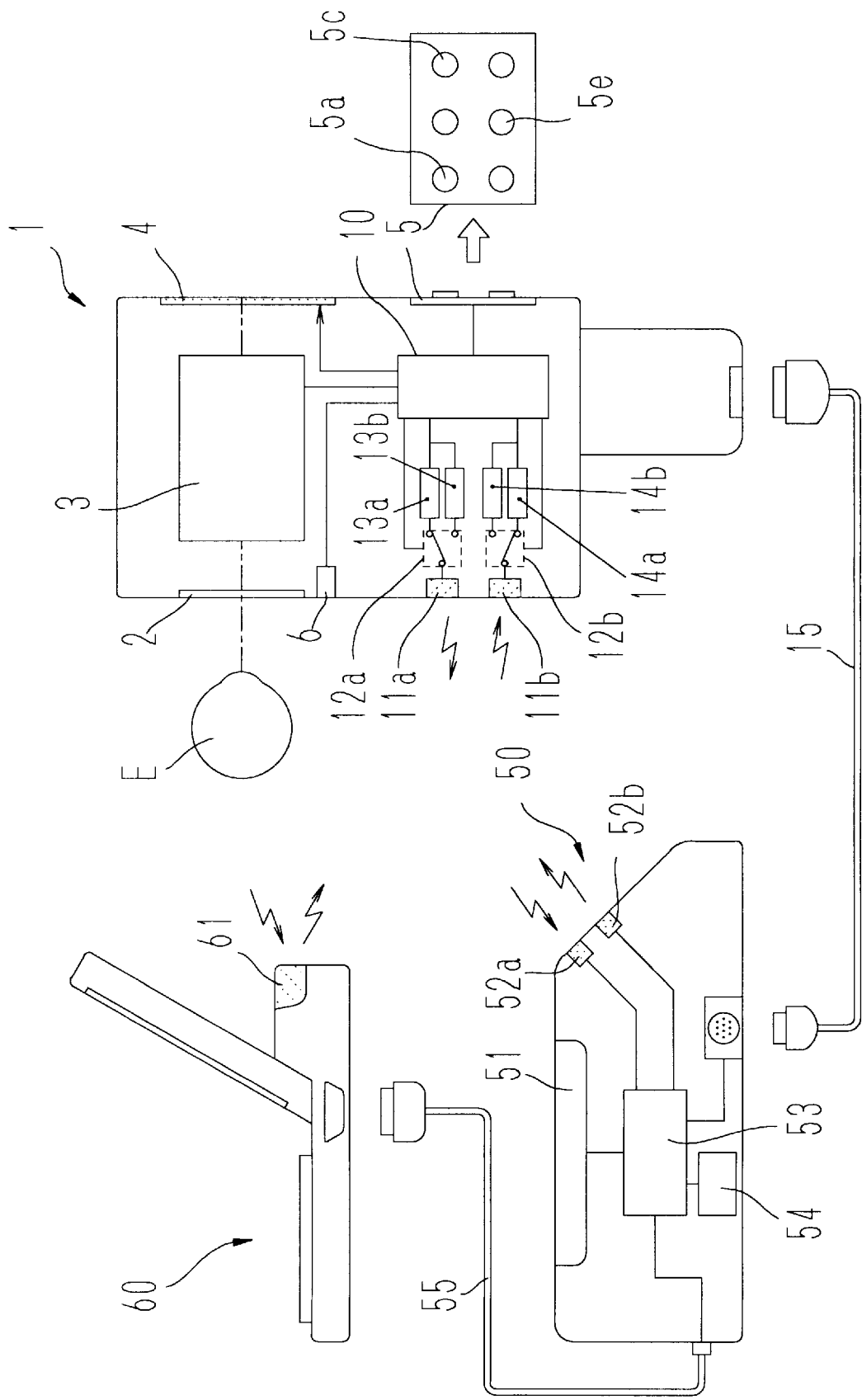
FIG. 1 is a view showing a schematic configuration of an apparatus of the preferred embodiment of the present invention.

A detailed description of one preferred embodiment of an ophthalmic apparatus embodying the present invention will now be given referring to the accompanying drawings. FIG. 1 is a view sowing a schematic configuration of the apparatus of this preferred embodiment.

Reference numeral 1 is a hand-held type measurement unit and mounted inside thereof is a measurement part 3 including a measurement optical system, an alignment optical system and an observation optical system therein for measuring a refractive power of an eye E to be examined through a measurement window 2. The observation optical system included in the measurement part 3 has a CCD camera for photographing an anterior portion of the eye E and picture signals generated thereby is outputted to a liquid crystal display 4 (hereinafter referred to as an LCD). An examiner performs alignment of the eye E while observing an image of the anterior portion of the eye, an image of an alignment luminance point and the like displayed on the LCD 4. The LCD 4 also displays measurement data and information to be announced to the examiner. As for the measurement optical system and the alignment optical system, widely known art may be adopted. Examples of the art which may be utilized are disclosed in Publication of Unexamined Japanese Patent Application No. HEI 10(1998)-108836 which corresponds to U.S. Pat. No. 5,907, 388 and in Publication of Unexamined Japanese Patent Application No. HEI 10(1998)-127581 which corresponds to U.S. Pat. No. 5,909,268.

Reference numeral 5 is a switch part having various switches and 6 is an R/L detecting part that irradiates detection light onto an examinee Is face to detect whether the eye E being examined is a right eye or a left eye based on the reflected light. 10 is a control part that controls overall operations of the measurement unit 1. The control part 10 judges suitability of alignment detection, performs arithmetic operations, controls each component based on signals from the measurement part 3. 11a is a light generating part and 11b is a light receiving part both of which are used in the case of carrying out data transmission between a printer 50, which is a peripheral unit, and an external computer 60 for control, which is provided with the IrDA standard communications facility, by way of optical communications. When transmitting data to, or from, the external computer 60, a switching circuit 12a connects a first modulation drive 13a for the IrDA standard and the light generating part 11a, and the switching circuit 12b connects a first demodulation drive 14a for the IrDA standard and the light receiving part 11b. When transmitting data to, or from, the printer 50, the switching circuit 12a connects a second modulation drive 13b for its specialized signal standard and the light generating part 11a, and the switching circuit 12b connects a second demodulation drive 14b for the specialized signal standard and the light receiving part 11b. In addition, communications with the printer 50 may be carried out by a cable 15.

The printer 50 comprises a printout part 51 for printing out measurement results, a light generating part 52a and a light receiving part 52b, both of which are for data transmission to, or from, the measurement unit 1 by way of optical communications, a control part 53 and a memory 54. The memory 54 stores format data for printing out and format data for external communications (the external computer 60), both of which will be described later. The printer 50 may be connected to the external computer 60 via a cable 55. The external computer 60 comprises a communications part 61 for infrared communications and sends/receives signals which meet the IrDA standard.

Operations of the apparatus having the above-mentioned configuration will be described hereinafter.

When performing a measurement, the examiner holds the measurement unit 1 with both hands so as to place the measurement window 2 in front of the eye E. An eye to be measured is discriminated automatically by the R/L detecting part 6, or the eye to be measured may be selected using a select switch 5a included in the switch part 5. For example, in the case of measuring a right eye first, the examiner performs alignment while observing an image of the anterior part of the eye E and an image of an alignment luminance point displayed on the LCD 4. Based on signals form the alignment optical system, the control part 10 judges suitability of the alignment condition and starts a measurement by the measurement optical system automatically when a predetermined requirement is satisfied. The measurement is repeated continuously until a predetermined number of measurement values are obtained (or the measurement is repeated for a predetermined number of times), and then a message is displayed on the LCD 4 to indicate that the measurement on the first eye is completed. When the measurement on the right eye is completed, the measurement on the left eye is performed in the same manner.

When the control part 10 determines that the measurements on both right and left eyes satisfy a predetermined condition to terminate the measurement (reference may be made to Publication of Unexamined Japanese Patent Application No. HEI 10(1998)-216088 which corresponds to U.S. Ser. No. 09/015,630 by the present applicant), the information is displayed on the LCD 4 and the data obtained by the measurement is automatically transmitted, in a form of optical signals, to the external peripheral unit. Here, the signal mode of the optical signals may be selected from a communications mode for the IrDA standard, a normal communications mode for the specialized standard, or a contentious communications mode which makes both possible. The selection is made previously from the menu displayed on the LCD 4 by manipulating the switch 5c. In accordance with the selection, the control part 10 switches the connection between the switching circuits 12a and 12b. In this embodiment, it is assumed that the normal communications mode is selected to transmit the data to the printer 50.

Figure 2:
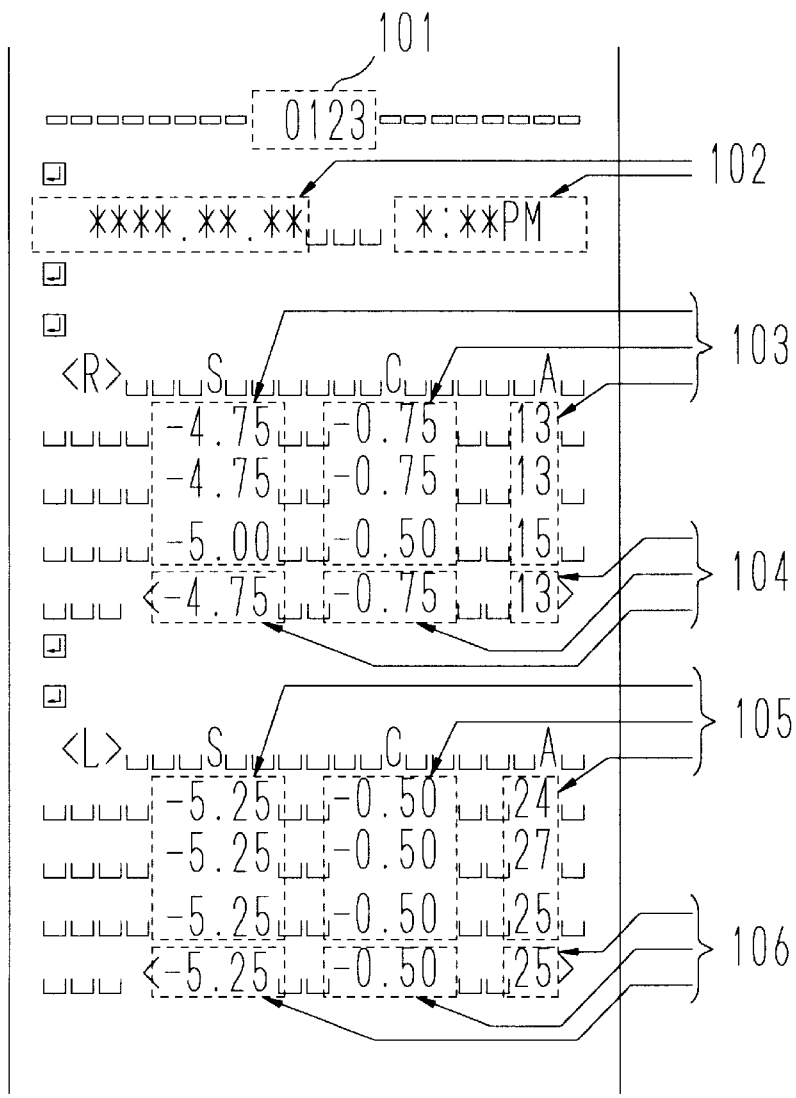
FIG. 2 is a view showing an example of a printout.

Descriptions are now given to communications between the measurement unit 1 and the printer 50. Since the memory 54 included in the printer 50 stores the format data for printout, the control part 10 of the measurement unit 1 transmits the measurement data without format data (unformatted measurement data). FIG. 2 is an example of printout that the printout part 51 outputs. In this example, the data transmitted from the measurement unit 1 is serial number (patient number) data 101, measurement date data 102, measurement value data 103 obtained by performing the measurement on the right eye three times, right eye typical value data 104, measurement value data 105 obtained by performing the measurement on the left eye three times, and left eye typical value data 106, all of which are enclosed in a box indicated by doted lines in the figure. Data such as other symbols, letters, line feeds, spaces to intervene between each numerals and the like are stored in the memory 54 as format data. Each of the data 101–106 is transmitted form the measurement unit 1 accompanying a code identifying to which part of the format the respective data corresponds. The control part 53 of the printer 50 expands each data into the printout format in accordance with the code, and then prints out the formatted data. Simultaneously, the control part 53 expands each data into the external communications format and then transmits the formatted data to the side of the external computer 60 via the cable 55.

As described above, the data that the measurement unit 1 transmits do not include the format data, and therefore the amount of data is decreased drastically. Since the amount of data is small, the data may be transmitted in short time and the possibility of transmission errors may be reduced. This is advantageous for the transmission via the cable 15, and it is particularly advantageous for the transmission by wireless communications in that it eliminates the need to adopt high-speed communications. As the result, the apparatus may remain relatively inexpensive and communications distance may be sufficiently lengthened.

The measurement unit 1 transmits such data as described above. In the case of wireless communications, there may be cases where the signals are not transmitted properly. To avoid such cases, the control part 10 repeats the data transmission for plurality of times (for example, ten times) at a certain time interval. Upon the transmission, an identification code is transmitted along with the data to indicate that the same set of the data is being transmitted. Upon receiving any set of the data among the data repeatedly transmitted plurality of times, the control part 53 of the printer starts to print out the data. The data received thereafter are ignored if they are identified as the same set of the data by the identification code. To print out the same set of data again, the examiner pushes a print switch 5e included in the switch part 5. Upon receiving the signal triggered by the print switch 5e, the control part 10 transmits the same set of the data with a different identification code.

Further, to improve the reliability, the apparatus of the present invention is provided with a bi-directional communications facility. The control part 53 of the printer 50 transmits a signal from the light generating part 52b to indicate that receiving the data is completed. Upon receipt of the signal via the light receiving part 11b, the control part 10 of the measurement unit 1 displays a completion-message on the LCD 4 and then automatically turns off the power.

Conversely, when an error occurs in receiving the data at the side of the printer 50 (the printer 50 (the light receiving part 52a) fails to receive the data), the control part 53 transmits a signal requesting retransmission of the data from the light generating part 52b. To determine whether the side of the printer 50 properly receives the data without an error, error checking data such as checksum may be added to the data transmitted from the measurement unit 1 so that the integrity of the received data can be checked. Upon receipt of the signal requesting retransmission, the control part 10 of the measurement unit 1 transmits the data again.

In case where the signal requesting retransmission is returned despite several attempts (for example five times), or where no signal indicating the completion is returned, there may be some errors on the side of the printer 50 (for example, a failure or the power is not on). In these cases, a message stating "print error" may be displayed on the LCD 4 or a warning sound may be generated to inform the examiner of the situation. In the cases where the cause of the failure is clearly identified (for example, a paper-out condition or a head-up condition), signals indicating the information about the cause of the failure are transmitted to the measurement unit 1 so as to display the cause on the LCD 4. With the apparatus applying wireless communications, it is often the case where the data are transmitted from a remote location from the printer 50. Even in the case, bi-directional communications as described above allow the examiner to be aware of the condition of the printer so that troubles may be handled easily.

In addition, when a relatively large amount of data needs to be transmitted (for example, when printing out the measurement data on a number of examinees all at a time after all the measurements) instead of printing out the measurement data upon completion of each measurement, the following should be done. Here, it should be noted that the control part 10 is provided with a memory capable of storing a large number of measurement data. When a preparation for data transmission is done, the examiner pushes the print switch 5e. First, the measurement unit 1 sends a message indicates a start of the transmission to the printer 50, and the printer 50, in response, returns a message permitting the transmission to the measurement unit 1. The measurement unit 1 starts the transmission after confirming that the message is returned from the printer 50. In the case where no message is returned, an error message is displayed on the LCD 4. This allows the examiner to be aware of the trouble (for example, the printer is not tuned on) and the like before transmitting a large amount of data. As the result, time spent on needless transmission is saved.

In the case where the format data for output needs to be changed due to the change made on the side of the measurement unit 1, the following should be done. The control part 10 of the measurement unit 1 stores format data for output along with a transmission program. When the format data stored in the memory 54 needs to be changed due to the change of the program made on the side of the measurement unit 1, the format data stored in the control part 10 also needs to be changed. If a mode of changing the output format is selected on a menu that is displayed on the LCD 4 by manipulating the switch 5c, the changed format data is allowed to be transmitted. If the print switch 5e is pushed when the measurement unit 1 is in the change mode, the changed format data is sent to the side of the printer 50 by optical communications or via the cable (upon the data transmission, an identification code is attached thereto, so that the side of the printer 50 can determine that the changed format data is being sent). Upon receipt of the data, the control part 53 of the printer 50 replace the format data for output stored in the memory 54 with the received data. This change may be made with the use of an external apparatus such as the external computer 60 or the like.

The measurement unit 1 may be a unit for measuring a corneal shape, instead of measuring an eye refractive power. Even in this case, if format data for corneal measurement is sent to replace the format data, the printer 50 may be commonly used without much trouble and the maintainability may be enhanced.

Further, when printout in a different format is desired (for example, different from the format shown in FIG. 2, when only a typical value needs to be outputted, when the refractive power of the measured eye needs to be graphically outputted, or when using the printer 50 also as a printer for a corneal shape measurement apparatus), the following is possible. The memory 54 previously stores a plurality of format data for output that corresponds to intended types of output format and the measurement unit 1 sends measured data along with an identification code indicating a type of the output format. The control part 53 of the printer 50 determines the format data to be used in accordance with the identification code. In the case of outputting the data graphically, one of graphics that are stored in the memory 54 in advance is selected and outputted.

Described hereinafter is the case where the measurement data is directly sent to the external computer 60. In this case, a communications mode for the IrDA standard is selected from the menu displayed on the LCD 4 by manipulating the switch 5c. When the measurement is completed (or when the print switch 5e is pushed), the light generating part 11a automatically sends an optical signal via the first modulation drive 13a. The side of the external computer 60 receives the optical signal via the communications part 61 and returns a signal indicating a completion of receiving the data after confirming that the data is successfully received or a signal indicating a data transmission error. The LCD 4 displays a message corresponding to the returned signal thereby to allow the examiner to confirm whether the measurement data has been successfully transmitted.

In addition, in the case where the measurement data needs to be transmitted to both the external computer 60 and the printer 50, a continuos communications mode is selected. In this mode, when the measurement is completed, the data being converted into signals comply with the IrDA standard are transmitted and then the data being converted into signals for the printer are transmitted (the order of the transmission may be reversed).

In the embodiment described above, the measurement data that the measurement unit 1 transmits does not include format data for output. However, when using a peripheral unit, such as a printer, which does not conform to the measurement unit 1 in order to format the measurement data, the measurement unit 1 may send the formatted measurement data in a conventional manner. In this case, a format mode is selected from the menu by manipulating the switch 5c and then the measurement data is transmitted.

The side of the printer 50 distinguishes the measurement data which has not been formatted by the identification code attached only to such data. The measurement data without the identification code is determined as the formatted data and printed out in the conventional manner. In this way, the printer 50 may be commonly used instead of making it for one dedicated use.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising a measurement unit and a peripheral unit each of which is contained in a separate housing, wherein the measurement unit includes:
   measurement means for measuring a characteristic of an eye to be examined; and
   sending means capable of sending a signal for sending measurement data obtained by the measurement means in an unformatted state for output, and
the peripheral unit includes:
   receiving means for receiving the signal sent by the sending means;
   output means for outputting the measurement data received by the receiving means;
   storage means for storing output format data used to format the measurement data upon output by the output means; and
   output control means for formatting the measurement data using the output format data and for controlling the output means so as to produce output.

2. The ophthalmic apparatus according to claim 1, wherein the peripheral unit further includes changing means for changing the output format data stored in the storage means, and
   the measurement unit further includes input means for inputting a change instruction signal to change the output format data.

3. The ophthalmic apparatus according to claim 2, wherein the measurement unit further includes:
   second storage means for storing output format data; and
   transmission control means for controlling the sending means so as to send the output format data stored in the second storage means in accordance with the change instruction signal, and
   the changing means replace the output format data stored in the storage means with the received output format data.

4. The ophthalmic apparatus according to claim 3, wherein the measurement unit further includes second changing means for changing the output format data stored in the second storage means based on the change instruction signal, and
   the transmission control means controls the sending means so as to send the output format data changed by the second changing means.

5. The ophthalmic apparatus according to claim 2, wherein the measurement unit further includes appending means for appending an identification code, based on the change instruction signal, to the measurement data to be sent,
   the storage means stores a plurality of types of output format data, and
   the changing means selects a type of the output format data to be used in accordance with the identification code appended to the received measurement data.

6. An ophthalmic apparatus comprising a measurement unit and a peripheral unit each of which is contained in a separate housing, wherein the measurement unit includes:
   measurement means for measuring a characteristic of an eye to be examined;
   completion determination means for determining whether a measurement is completed;
   sending means capable of sending a signal via wireless communications for sending measurement data obtained by the measurement means; and
   transmission control means for controlling the sending means so as to send the measurement data automatically when the completion determination means determines that the measurement is completed, and
the peripheral unit includes:
   receiving means capable of wireless communications for receiving the signal sent by the sending means; and output means for outputting the measurement data received by the receiving means.

7. The ophthalmic apparatus according to claim 6, wherein the transmission control means controls the sending means so as to send the same measurement data plurality of times at a predetermined interval, and the peripheral unit further includes:
determination means for determining whether or not the received measurement data is the same as the measurement data which has been received; and
control means for controlling the output means so as not to output the measurement data that is determined by the determining means to be the same as the measurement data which has been received.

8. The ophthalmic apparatus according to claim 7, wherein the transmission control means further includes appending means for appending an identification code to the same measurement data so that the same measurement data is identified.

9. The ophthalmic apparatus according to claim 6, wherein the peripheral unit further includes second sending means for sending a response signal when the receiving means receives the measurement data, and the measurement unit further includes:
second receiving means for receiving the response signal sent by the second sending means; and
informing means for informing an examiner of a receiving state of the second receiving means.

10. The ophthalmic apparatus according to claim 6, wherein the peripheral unit further includes second sending means for sending a signal requesting retransmission of the measurement data when the receiving means does not complete receiving of the measurement data within a predetermined time or when there is an error in the received measurement data, the measurement unit further includes second receiving means for receiving the signal requesting retransmission sent by the second sending means, and
the transmission control means instructs the sending means to retransmit the measurement data when the second receiving means receives the signal requesting retransmission.

11. The ophthalmic apparatus according to claim 10, wherein the measurement unit further includes informing means for informing an examiner of a receiving state of the second receiving means.

12. The ophthalmic apparatus according to claim 6, wherein the measurement unit further includes:

transmission start announcing means for sending a transmission start signal automatically when the completion determination means determines that the measurement is completed; and
second receiving means for receiving the signal,
the peripheral unit further includes second sending means for sending a signal to permit transmission when the receiving means receives the transmission start signal, and
the transmission control means instructs the sending means to send the measurement data when the second receiving means receives the signal to permit transmission.

13. An ophthalmic apparatus comprising a measurement unit and a peripheral unit each of which is contained in a separate housing, wherein the measurement unit includes:

measurement means for measuring a characteristic of an eye to be examined;
sending means capable of sending a signal via wireless communications for modulating and sending measurement data obtained by the measurement means to comply with a plurality of types of communications standards; and
select means for selecting a type of the communications standard to be used in transmission, and the peripheral unit includes:
receiving means capable of wireless communications for receiving the signal sent by the sending means; and
output means for outputting the measurement data received by the receiving means.

14. The ophthalmic apparatus according to claim 13, wherein the plurality of types of the communications standards include the IrDA standard.

15. The ophthalmic apparatus according to claim 13, wherein the sending means and the receiving means are means for optical communications, the sending means includes a light generating part and a plurality of modulation drives each of which meets a different communications standard, and select means includes:
a select switch for selecting a communications standard to be used; and
a send switching circuit for connecting the light generating part to one of the modulation drives in accordance with an input signal from the select switch.

16. The ophthalmic apparatus according to claim 15, wherein the peripheral unit further includes second sending means for sending a response signal, the measurement unit includes second receiving means, provided with a light receiving part and a plurality of demodulation drives each of which meets a different communications standard, for receiving the response signal, and
the select means includes a receive switching circuit for connecting the light receiving part to one of the demodulation drives in accordance with the input signal from the select switch.

* * * * *

UNITED STATES PATENT AND TRADEMARK OFFICE
CERTIFICATE OF CORRECTION

PATENT NO.: 6,123,423

DATED: September 26, 2000

INVENTOR(S): Isogai et al.

It is certified that an error appears in the above-identified patent and that said Letters Patent is hereby corrected as shown below:

Title Page, number [56], under --"US PATENT DOCUMENTS"--, insert omitted references as follows:

--5,907,388  5/1999   Fujieda
5,909,268   6/1999   Isogai et al.
5,940,165   8/1999   Isogai et al.
5,565,939   10/1999  Fujieda --

Title Page, number [56], insert --FOREIGN PATENT DOCUMENTS--, and insert thereunder omitted references as follows:

-- HEI 10-108836  4/1998   JP
HEI 10-127581    5/1998   JP
HEI 10-216088    8/1998   JP
HEI 7-116120     5/1995   JP
HEI 7-265269     10/1995  JP
HEI 8-191796     7/1996   JP
HEI 5-154103     6/1993   JP --

Signed and Sealed this

Eighth Day of May, 2001

Attest:

NICHOLAS P. GODICI

Attesting Officer    Acting Director of the United States Patent and Trademark Office

UNITED STATES PATENT AND TRADEMARK OFFICE
CERTIFICATE OF CORRECTION

PATENT NO. : 6,123,423
DATED : September 26, 2000
INVENTOR(S) : Naoki Isogai et al.

Page 1 of 1

It is certified that error appears in the above-identified patent and that said Letters Patent is hereby corrected as shown below:

Claim 7, Column 9,
Line 10, before "control means", insert --output--.

Signed and Sealed this

Third Day of July, 2001

Attest:

NICHOLAS P. GODICI
Attesting Officer
Acting Director of the United States Patent and Trademark Office